United States Patent
Munro et al.

(10) Patent No.: US 10,405,754 B2
(45) Date of Patent: Sep. 10, 2019

(54) STANDARDIZED ORAL HEALTH ASSESSMENT AND SCORING USING DIGITAL IMAGING

(71) Applicants: Cindy L. Munro, Apollo Beach, FL (US); Paula Louise Cairns, Safety Harbor, FL (US); Xusheng Chen, Tampa, FL (US); Gwendolyn J. Good, Sarasota, FL (US); Kevin Edward Kip, Tampa, FL (US)

(72) Inventors: Cindy L. Munro, Apollo Beach, FL (US); Paula Louise Cairns, Safety Harbor, FL (US); Xusheng Chen, Tampa, FL (US); Gwendolyn J. Good, Sarasota, FL (US); Kevin Edward Kip, Tampa, FL (US)

(73) Assignee: University of South Florida, Tampa, FL (US)

( * ) Notice: Subject to any disclaimer, the term of this patent is extended or adjusted under 35 U.S.C. 154(b) by 296 days.

(21) Appl. No.: 15/450,925

(22) Filed: Mar. 6, 2017

(65) Prior Publication Data

US 2017/0172418 A1    Jun. 22, 2017

Related U.S. Application Data

(63) Continuation-in-part of application No. 15/366,741, filed on Dec. 1, 2016, now abandoned.
(Continued)

(51) Int. Cl.
*G06T 7/00* (2017.01)
*A61B 5/00* (2006.01)
(Continued)

(52) U.S. Cl.
CPC ........ *A61B 5/0088* (2013.01); *A61B 1/00009* (2013.01); *A61B 1/24* (2013.01);
(Continued)

(58) Field of Classification Search
CPC ....... A61B 5/0088; A61B 1/24; A61B 5/1032; A61B 5/7264; A61B 1/00009;
(Continued)

(56) References Cited

U.S. PATENT DOCUMENTS

| 8,110,178 B2 | 2/2012 | Fujikawa et al. | |
|---|---|---|---|
| 2003/0161401 A1* | 8/2003 | Shen | G06T 3/4084 375/240.16 |

(Continued)

OTHER PUBLICATIONS

Rosa GM, Elizondo ML. New portable system for dental plaque measurement using a digital single-lens reflex camera and image analysis: Study of reliability and validation. Journal of Indian Society of Periodontology. 2015;19(3):279-284.
(Continued)

*Primary Examiner* — Zhihan Zhou
(74) *Attorney, Agent, or Firm* — Smith & Hopen, P.A.; Paul Murty

(57) ABSTRACT

System and methodology objectively capture clinical data on oral health and provide standardized scoring for quantifying oral health. The process of capturing clinical data is based on use of an intraoral camera with imaging software that has the capacity to capture digital images of all tooth surfaces. Digital plaque data are collected in a standardized manner per tooth, and with the ability to select optimal frames for analysis. Data are extracted per tooth into a software program. Color classification of each pixel is determined by the software program using an algorithm that makes use of red/green/blue color code combinations. These classifications are then quantitatively used within the soft-
(Continued)

ware program and separate algorithms that automatically generate a range of oral health scoring techniques.

11 Claims, 8 Drawing Sheets
(3 of 8 Drawing Sheet(s) Filed in Color)

Related U.S. Application Data

(60) Provisional application No. 62/261,631, filed on Dec. 1, 2015.

(51) Int. Cl.
| | | |
|---|---|---|
| *H04N 7/18* | (2006.01) | |
| *A61B 1/24* | (2006.01) | |
| *A61B 5/103* | (2006.01) | |
| *G06T 7/90* | (2017.01) | |
| *A61B 1/00* | (2006.01) | |
| *G16H 40/63* | (2018.01) | |
| *A61C 9/00* | (2006.01) | |

(52) U.S. Cl.
CPC .......... *A61B 5/1032* (2013.01); *A61B 5/7264* (2013.01); *A61C 9/0053* (2013.01); *G06T 7/0012* (2013.01); *G06T 7/90* (2017.01); *G16H 40/63* (2018.01); *H04N 7/183* (2013.01); *A61B 2576/00* (2013.01); *G06T 2207/10024* (2013.01); *G06T 2207/30036* (2013.01)

(58) Field of Classification Search
CPC .. A61B 2576/00; H04N 7/183; G06T 7/0012; G06T 2207/30036; G06T 2207/10024; G06T 7/90; A61C 9/0053; G16H 40/63
See application file for complete search history.

(56) References Cited

U.S. PATENT DOCUMENTS

| | | | | |
|---|---|---|---|---|
| 2005/0244794 | A1* | 11/2005 | Kemp | G06T 7/0012 433/217.1 |
| 2010/0183523 | A1* | 7/2010 | Wagner | A61Q 11/00 424/50 |
| 2010/0279248 | A1* | 11/2010 | Mourad | A61B 5/0534 433/29 |
| 2010/0280793 | A1 | 11/2010 | Wilhelm et al. | |
| 2011/0216409 | A1* | 9/2011 | Stutes | G02B 27/00 359/507 |
| 2011/0301441 | A1* | 12/2011 | Bandic | A61B 5/0059 600/306 |
| 2014/0118427 | A1* | 5/2014 | Buckley | G09G 3/36 345/691 |
| 2014/0199651 | A1* | 7/2014 | Adachi | A61C 17/20 433/27 |

OTHER PUBLICATIONS

Michael G McGrady, Roger P Ellwood, Andrew Taylor, Anne Maguire, Michaela Goodwin, Nicola Boothman and Iain A Pretty, Evaluating the use of fluorescent imaging for the quantification of dental fluorosis, BMC Oral Health (2012), 12, 47:1-8.
Pretty I A; Edgar W M; Smith P W; Higham S M, Quantification of dental plaque in the research environment, Journal of dentistry (2005), 33, (3), 193-207.
Lupita Jocelin Reyes Silveyra, Investigations on Automated Methods for Dental Plaque Detection, A thesis submitted to The University of Birmingham for the degree of Doctor of Philosophy, School of Dentistry College of Medical and Dental Sciences The University of Birmingham Sep. 2011, pp. 1-387.
International Search Report and Written Opinion notification dated May 30, 2017 for corresponding PCT International Application No. PCT/US17/21367, International Filing Date Mar. 8, 2017.
International Preliminary Report on Patentability with an electronic notification dated Jun. 13, 2019 for corresponding PCT International Application No. PCT/US17/21367, International Filing Date Mar. 8, 2017.

* cited by examiner

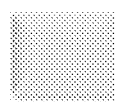 *Perio Mode*
Dental plaque
- Orange to yellow: Tatar(Calculus)
- Grainy & White: Plaque
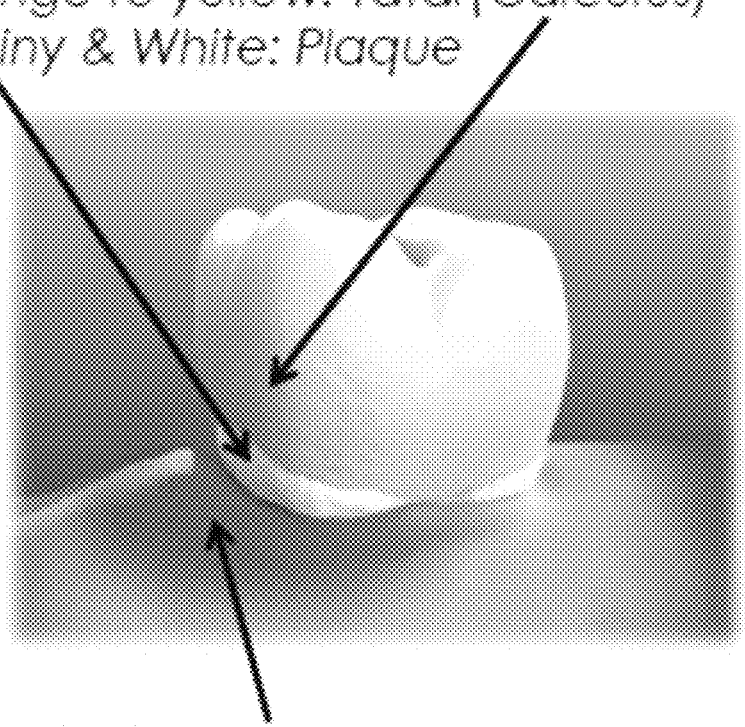
Gingival inflammation
- Purplish pink to Magenta: Inflammation
- Pink: Healthy gum
*FIG. 4B*

```
library(EBImage)
f = system.file("images", "image.jpg", package="EBImage")
img = readImage(f)
yellowratio = function(img = img)
{ length = dim(img)[1]
  width = dim(img)[2]
  count = 0
  discount = 0
  for (i in 1:length)
   { print(i)

for (j in 1: width)
    {
    if (img[][i,j,3] == 1)
       discount = discount + 1
    else if (img[][i,j,1] >= 0.75*img[][i,j,2] & img[][i,j,1] <= 2.5*img[][i,j,2] & img[][i,j,2] >
1.2*img[][i,j,3] & img[][i,j,1] > 1.2*img[][i,j,3])
       count = count + 1
    }
   } elenum = (length * width) - discount
  ratio = count/elenum
  return (ratio)

}
yellowratio(img)
```

*FIG. 5*

| | | | |
|---|---|---|---|
| Normal | Normal | Normal | Normal |
| Normal | Normal | Normal | Normal |
| Normal | Normal | Normal | Normal |
| Normal | Normal | Normal | Normal |
| Normal | Normal | Normal | Normal |
| Plaque | Normal | Normal | Normal |
| Normal | Normal | Normal | Normal |
| Normal | Normal | Normal | Normal |
| Normal | Normal | Normal | Normal |
| Plaque | Normal | Normal | Normal |
| Plaque | Plaque | Normal | Normal |
| Normal | Normal | Normal | Normal |
| Normal | Normal | Normal | Normal |
| Plaque | Normal | Normal | Normal |
| Plaque | Plaque | Normal | Normal |
| Plaque | Plaque | Plaque | Normal |

*FIG. 6*

R code:

> x5 <- sample(1:4271,50,replace=F)

STANDARDIZED ORAL HEALTH ASSESSMENT AND SCORING USING DIGITAL IMAGING

CROSS-REFERENCE TO RELATED APPLICATIONS

This nonprovisional application is a continuation-in-part of U.S. Nonprovisional patent application Ser. No. 15/366,741, entitled "Standardized Oral Health Assessment and Scoring Using Digital Imaging", filed Dec. 1, 2016, which claims priority to U.S. Provisional Patent Application No. 62/261,631, entitled "Standardized Oral Health Assessment and Scoring Using Digital Imaging", filed Dec. 1, 2015, all of which are incorporated herein by reference in their entireties.

FEDERALLY SPONSORED RESEARCH OR DEVELOPMENT

This invention was made with government support under Grant Number R01 NR007652 awarded by the National Institutes of Health. The government has certain rights in the invention.

BACKGROUND OF THE INVENTION

1. Field of the Invention

This invention relates, generally, to oral health assessments. More specifically, it relates to use of digital imaging to standardize, assess, and score oral health in a subject.

2. Brief Description of the Prior Art

Despite its prominent position in bedside care, there is little evidence to judge the benefits or associated risks of nurse-administered tooth brushing for mechanically ventilated adults, and the optimal frequency of tooth brushing in the critically ill has never been experimentally determined. Traditional methods for scoring oral health, including both tooth (e.g., plaque burden) and gum (e.g., inflammation) health, have relied upon visual examination by skilled professionals, including dental hygienists. Given the relatively subjective nature of this process, measurement of oral health is suboptimal for a number of reasons including, but not limited to: time burden, lack of reliability within and between assessors, lack of universal standardized scoring algorithms, and computational complexity in attempting to score oral health on multiple dimensions, such as simultaneous assessment of age and extent of plaque burden.

Attempts have been made at evaluating and quantifying plaque and oral health. Examples include U.S. Pat. No. 8,110,178; U.S. patent application Ser. No. 12/832,652; U.S. patent application Ser. No. 11/662,346; Lupita Jocelin Reyes Silveyra, Investigations on Automated Methods for Dental Plaque Detection, A thesis submitted to The University of Birmingham for the degree of Doctor of Philosophy, School of Dentistry College of Medical and Dental Sciences, The University of Birmingham, September 2011; Pretty I A, et al., Quantification of dental plaque in the research environment, Journal of dentistry (2005), 33, (3), 193-207, ISSN: 0300-5712; Michael G McGrady, et al., Evaluating the use of fluorescent imaging for the quantification of dental fluorosis, BMC Oral Health (2012), 12, 47; and Rosa G M, et al., New portable system for dental plaque measurement using a digital single-lens reflex camera and image analysis: Study of reliability and validation. Journal of Indian Society of Periodontology. 2015; 19(3):279-284. doi:10.4103/0972-124X.152415. However, none provide a standardized and objective system for assessing oral health.

Accordingly, what is needed for both for clinicians and researchers is a reliable, user-friendly, and fully objective and standardized methodology and system for quantifying and scoring oral health. However, in view of the art considered as a whole at the time the present invention was made, it was not obvious to those of ordinary skill in the field of this invention how the shortcomings of the prior art could be overcome.

While certain aspects of conventional technologies have been discussed to facilitate disclosure of the invention, Applicants in no way disclaim these technical aspects, and it is contemplated that the claimed invention may encompass one or more of the conventional technical aspects discussed herein.

The present invention may address one or more of the problems and deficiencies of the prior art discussed above. However, it is contemplated that the invention may prove useful in addressing other problems and deficiencies in a number of technical areas. Therefore, the claimed invention should not necessarily be construed as limited to addressing any of the particular problems or deficiencies discussed herein.

In this specification, where a document, act or item of knowledge is referred to or discussed, this reference or discussion is not an admission that the document, act or item of knowledge or any combination thereof was at the priority date, publicly available, known to the public, part of common general knowledge, or otherwise constitutes prior art under the applicable statutory provisions; or is known to be relevant to an attempt to solve any problem with which this specification is concerned.

BRIEF SUMMARY OF THE INVENTION

The long-standing but heretofore unfulfilled need for an improved method of assessing oral health is now met by a new, useful, and nonobvious invention.

In an embodiment, the current invention is a method of assessing oral health in a patient or subject. The method includes capturing or recording the frames of substantially all buccal, occlusal, and lingual surfaces in the subject's set of teeth, using a suitable intraoral camera. The frames are imported into an image processing software program that is implemented on a computing device. The frames are processed on the software program to generate images of the teeth to be analyzed. The color of at least a plurality of the frames/images are analyzed and classified to determine presence of yellow color, wherein yellow color indicates presence of plaque. Results of the color analysis are scored to objectively and quantitatively assess the subject's oral health.

Optionally, a dental barrier can be positioned over a lens of the intraoral camera, and a camera tip of the intraoral camera is positioned over the dental barrier.

The frames captured by the intraoral camera may be either photographs taken by the camera or video recordings taken by the camera. When the frames are photographs, the subject's teeth can be divided into a plurality of sections, including an upper right section, a lower right section, an upper middle section, a lower middle section, an upper left section, and a lower left section. Further, when the frames are photographs, processing the frames can be performed by cropping each image such that the image includes the targeted tooth, and the resolution of the image can be lowered to a percentage of about 50 or less.

In other embodiments when the frames are photographs, the color of the image is analyzed and classified by classifying the color of each pixel of the image. Further, each pixel is classified using RGB color code combinations, wherein a three-dimensional point (x, y, z) defines the color of each pixel. Still further, the step of analyzing and classifying color is further performed by dividing each color dimension of the RGB color code combinations into four (4) categories: (0, 64), (64, 128), (128, 192), and (192, 255). A middle point is selected in each category to be representative of the corresponding category. All categories are then cored to determine when yellow color is present on each pixel. When this is done, it was found that yellow color is present on each pixel when a value of a red dimension is between about 0.75 times of a value of a green dimension and about 2.5 times of the value of the green dimension, and when the values of the green and red dimensions are at least about 1.2 times a value of a blue dimension. Optionally, scoring the results of the color analysis can include calculating a percentage of yellow color in an image by dividing the number of yellow pixels by the total number of pixels in the image.

As noted previously, the frames may be video recordings. In this case, the subject's teeth can be divided into a plurality of quadrants, including an upper right quadrant, a lower right quadrant, an upper left quadrant, and a lower left quadrant. Video should be captured and recorded in at least one upper quadrant and at least one lower quadrant. Optionally, the following order can be used to take video in each quadrant: capturing and recording video of the buccal surfaces in the quadrant, followed by capturing and recording video of the occlusal surfaces in the quadrant, followed by capturing and recording video of the lingual surfaces in the quadrant, and followed by repeating the foregoing steps in another quadrant.

In other embodiments when video recordings are used, processing the frames includes extracting single still frame digital images of the tooth surfaces from the video recording. Optionally, each image is cropped, and a resolution of the image can be lowered to a percentage of about 50 or less. The color of the image is analyzed and classified by classifying the color of each pixel of the image. Further, each pixel is classified using RGB color code combinations, wherein a three-dimensional point (x, y, z) defines the color of each pixel. Still further, the step of analyzing and classifying color is further performed by dividing each color dimension of the RGB color code combinations into four (4) categories: (0, 64), (64, 128), (128, 192), and (192, 255). A middle point is selected in each category to be representative of the corresponding category. All categories are then cored to determine when yellow color is present on each pixel. When this is done, it was found that yellow color is present on each pixel when a value of a red dimension is between about 0.75 times of a value of a green dimension and about 2.5 times of the value of the green dimension, and when the values of the green and red dimensions are at least about 1.2 times a value of a blue dimension. Optionally, scoring the results of the color analysis can include calculating a percentage of yellow color in an image by dividing the number of yellow pixels by the total number of pixels in the image.

Optionally, when video recordings are taken, a plurality of frames from all frames can be randomly selected prior to processing the frames on the software program. This random selection can be performed with or without criteria for the random selection.

In a separate embodiment, the current invention is a method of assessing oral health in a patient or subject, comprising any one or more—or even all—of the foregoing steps.

These and other important objects, advantages, and features of the invention will become clear as this disclosure proceeds.

The invention accordingly comprises the features of construction, combination of elements, and arrangement of parts that will be exemplified in the disclosure set forth hereinafter and the scope of the invention will be indicated in the claims.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

For a fuller understanding of the invention, reference should be made to the following detailed description, taken in connection with the accompanying drawings, in which:

FIG. 4B is a schematic of "perio mode" of the ACTEON SOPROCARE intraoral camera.

FIG. 5 depicts the R code for obtaining the final plaque percentage for the tooth.

FIG. 6 is a chart depicting color samples that can be classified as 'yellow' color (plaque) or non-yellow color (normal).

FIG. 7 depicts the R code for randomly selecting fifty (50) numbers/frames from a video recording.

DETAILED DESCRIPTION OF THE PREFERRED EMBODIMENT

In the following detailed description of the preferred embodiments, reference is made to the accompanying drawings, which form a part thereof, and within which are shown by way of illustration specific embodiments by which the invention may be practiced. It is to be understood that other embodiments may be utilized and structural changes may be made without departing from the scope of the invention.

As used in this specification and the appended claims, the singular forms "a", "an", and "the" include plural referents unless the content clearly dictates otherwise. As used in this specification and the appended claims, the term "or" is generally employed in its sense including "and/or" unless the context clearly dictates otherwise.

Figure 1:
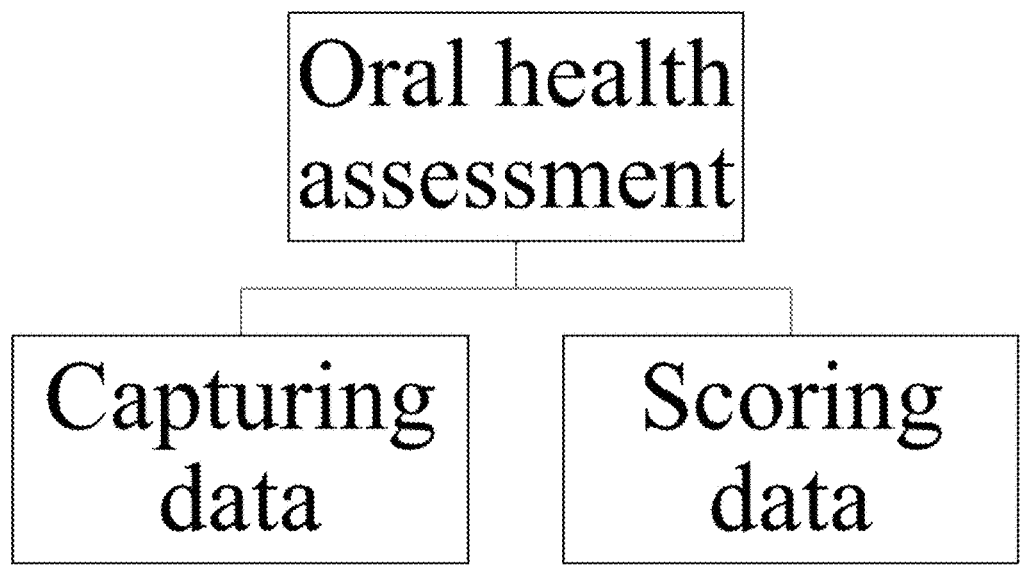
FIG. 1 is a flowchart depicting the steps of oral health assessment, according to an embodiment of the current invention.

In an embodiment, the current invention uses digital imaging technology to objectively capture clinical data on oral health, and then provides standardized scoring methodology for quantifying oral health. The methodology is applicable to persons in clinical settings (including hospitalized patients) as well as the general population. Generally, it involves two (2) stages (see FIG. 1): the process of capturing clinical data by use of digital imaging technology, and the process of standardized scoring of oral health data.

Figure 2:
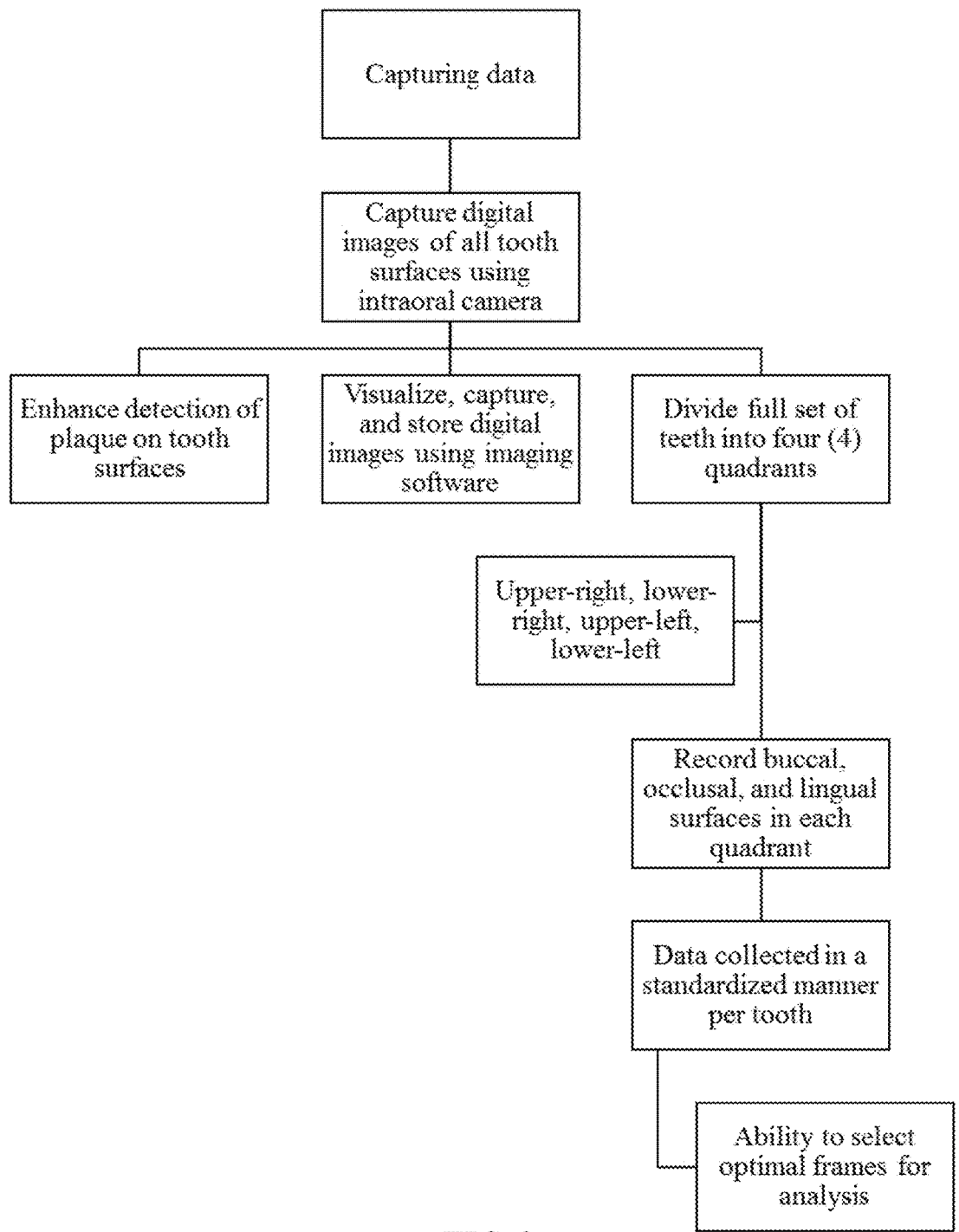
FIG. 2 is a flowchart depicting the steps of capturing data, according to an embodiment of the current invention.

Capturing Clinical Data (FIG. 2)

The process of capturing clinical data on oral health is based on the use of a conventional intraoral camera (e.g., ACTEON SOPROCARE Diagnostic/Clinical Intraoral Cameras) that has the capacity to capture digital images of all tooth surfaces in white light within and outside of dental laboratory settings. Any suitable intraoral camera is contemplated herein. Data from the digital images are used to enhance the detection of plaque on tooth surfaces, which are difficult to directly observe and score by a dental hygienist. Imaging software (e.g., ACTEON SOPRO Imaging Software) is used in conjunction with the camera to visualize, capture, and store each subject's digital image recording.

The process of digital imaging divides the subject's full set of teeth into four (4) quadrants. These quadrants include an upper right quadrant, lower right quadrant, upper left quadrant, and lower left quadrant. The recording of buccal, occlusal, and lingual surfaces of each quadrant in video-mode is significantly more effective and efficient than taking multiple still frame images at the bedside. Each tooth's digital plaque data is collected in a standardized manner, and with the ability to select optimal frames for analysis.

Figure 3:
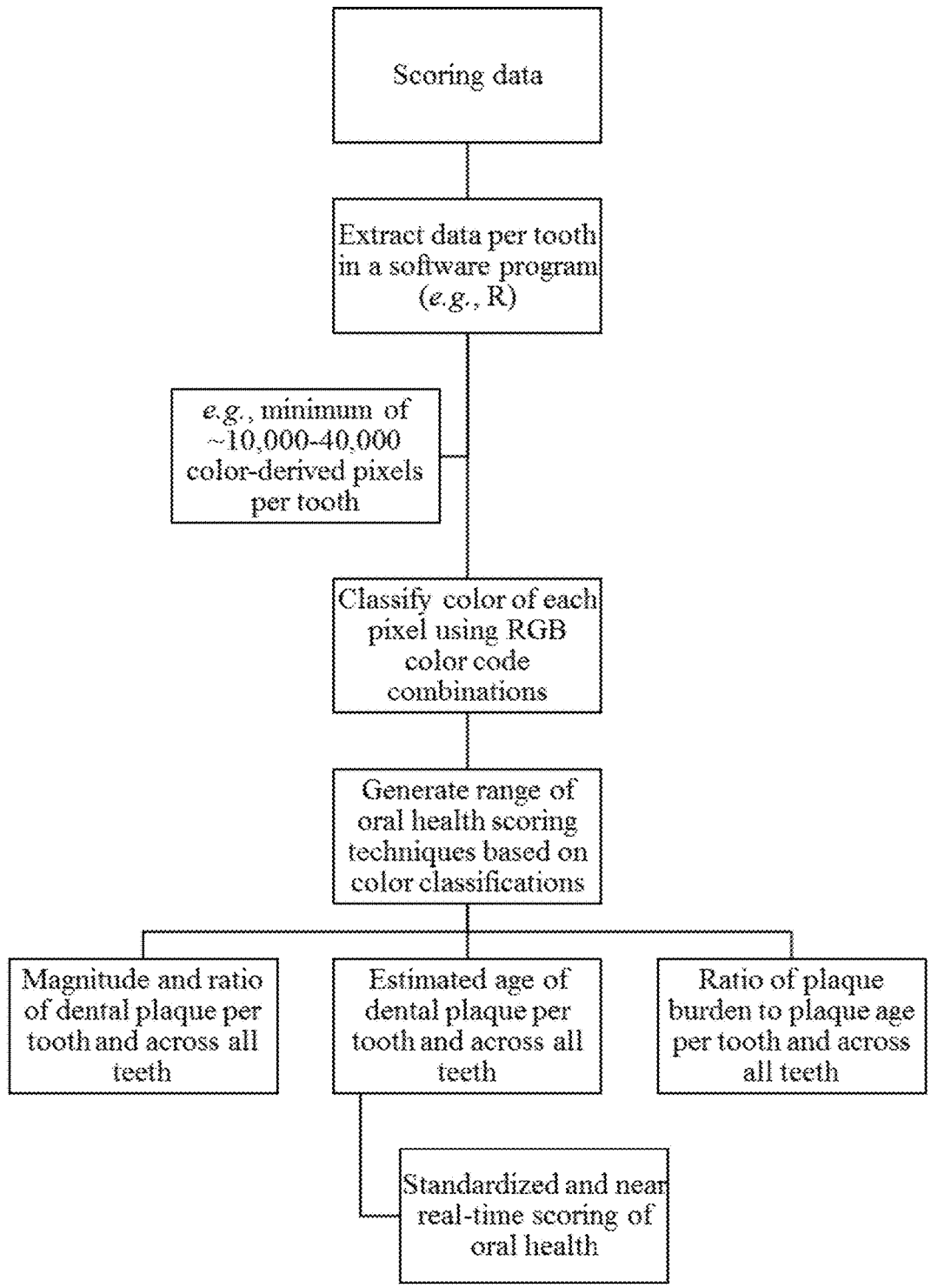
FIG. 3 is a flowchart depicting the steps of scoring data, according to an embodiment of the current invention.

Scoring Clinical Data (FIG. 3)

When not utilizing intraoral cameras, dental plaque burden is conventionally scored by visual examination by use of the University of Mississippi Oral Hygiene Index (UM-OHI). Using visual examination, for the ten (10) sections of each tooth, plaque is scored as present (value of 1) versus absent (value of 0). Thus, the maximum plaque score per tooth is 10. The mean plaque score for the subject is calculated by dividing the total score by number of teeth. By way of contrast, with the intraoral camera and imaging software, according to certain embodiments of the current invention, each tooth's data is extracted into a software program, such as but not limited to R, and with a minimum of about 10,000-40,000 color-derived pixels per tooth.

The color classification of each pixel is determined by the software program using an algorithm that makes use of red/green/blue (RGB) color code combinations. These classifications are then calculated quantitatively within the software program, and a separate algorithm automatically generates a range of oral health scoring techniques. These include, but are not limited to: (i) magnitude (and ratio) of dental plaque per tooth and across all teeth; (ii) estimated age of dental plaque per tooth and across all teeth; and (iii) ratio of plaque burden to plaque age per tooth and across all teeth. The process of oral health scoring is set up such that after appropriate selection of digital images has been achieved with use of the intraoral camera, and after these data have been imported into the computer coding language/program (e.g., R), only a few key strokes are required to compile and execute the algorithmic code, thereby resulting in standardized and near real-time scoring of oral health.

EXAMPLE

Capturing Data

A conventional intraoral camera, such as SOPROCARE by ACTEON used herein, illuminates dental tissue with a wavelength of light between 440 nm and 680 nm. Exposed tissue absorbs the energy and reflects it in florescent form. The handheld intraoral camera can be connected to a computing device wirelessly or by way of a video cable. If a wired connection is used, the video cable is connected to both the intraoral camera and the computing device. The dental camera electrical supply is directly powered through the computer USB port. The voltage powering the camera is of continuous 5 V low voltage type (0.5 A). On the computing device, imaging software, such as SOPRO Imaging software, such as SOPRO V2.3 used herein, is required to visualize, capture, and store video and digital images taken by the intraoral camera. Upon initiating the imaging software, a procedure file was created for each subject in order to record and store the digital images. The computing device was placed near the subject's head during the procedure in order to use the monitor as the display screen to visually guide the intraoral camera over each tooth surface. The camera focus ring was set to intraoral mode for video capture and/or camera digital image capture.

Figure 4A:
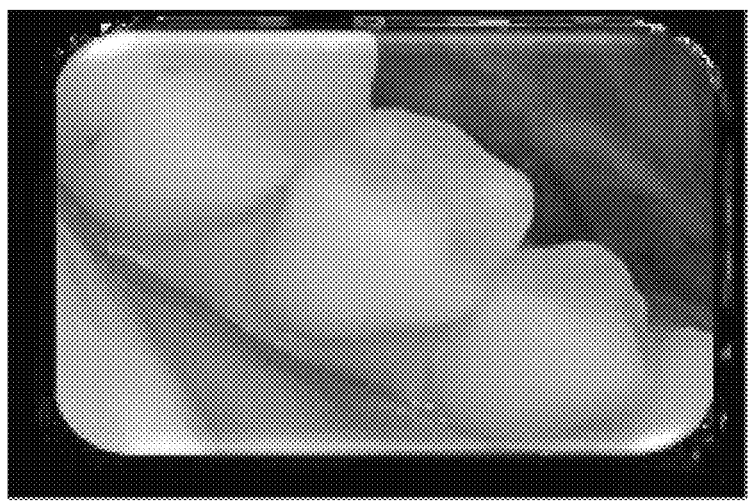
FIG. 4A is an image of a tooth using the "intra-oral" setting of the intraoral camera.

The mode on the intraoral camera was then set to the appropriate setting. On the ACTEON SOPROCARE camera for example, there is a rotating focus ring used to focus from "0" to infinite. The "intra-oral" (1-5 teeth) setting captures an image that is 5 mm to 30 mm from the camera. This setting was used for both video and camera digital image capture. See FIG. 4A. Additionally, the ACTEON SOPROCARE camera has a "perio mode", which is a fluorescent mode that is associated with chromatic amplification to highlight dental plaque using ultraviolet light. This "perio mode" revealed both old and new plaque in various stages. New plaque was interpreted as a white color, while older plaque was interpreted as yellow or orange colors depending on its mineralization. See FIG. 4B. Perio mode was used herein to capture video and camera digital images.

A disposable dental barrier can be placed over the camera lens, followed by the optional placement of a camera tip over the dental barrier. The camera tip enables displacement of ambient lighting. In the event of an anatomically small mouth or an oral cavity that is minimized due to facial and tongue swelling, the intraoral camera can capture adequate digital images of dental plaque without using a camera tip.

Mouth props may be used to assist subjects with or without an endotracheal tube to keep the mouth open wide enough for movement of the intraoral camera during the procedure. The mouth prop would be placed on the opposite side of the mouth being recorded.

At this point, the intraoral camera can initiate video or camera digital image recordings. For video recordings, the subject's full set of teeth were visualized in four quadrants. These quadrants included an upper right quadrant, lower right quadrant, upper left quadrant, and lower left quadrant. The speed of video digital imaging decreases the amount of subject burden. Pausing 1 to 2 seconds over each tooth surface will enhance the quality of still frame images to be produced from the video at a later time. In preparation for unforeseen events that make it impossible to complete digital imaging of all four quadrants, it is more representative data of oral health to obtain one-half of a full set of digital images from an upper quadrant and lower quadrant than one-half of a full set of digital images that is either both upper quadrants or both lower quadrants. Recording tooth surfaces closest to the endotracheal tube is recommended to be completed last, in case the subject is susceptible to coughing or gagging with incidental movement of the endotracheal tube. Placing the intraoral camera close to the mouth at the initiation of image recording and again at the conclusion of image recording can assist in protecting the subject's identity by avoiding incidental recording of a camera-facing headshot.

These video recordings can be obtained in any suitable way. The following is an exemplary step-by-step methodology for taking these recordings. First, the technician or other member of the medical team (herein the "operator") can lift the subject's upper lip with a free hand to expose the full buccal surface of the central and lateral incisor areas. The camera is held steady over the subject's first available upper quadrant front tooth for 1-2 seconds and over each buccal tooth surface thereafter, moving the camera over the central and lateral incisor area. Alternatively, the camera does not need to stop or be held steady for 1-2 seconds over each tooth surface; rather, the camera can simply take a continuous video along the rows of teeth, and frames can be extracted from that video, as will become clearer as this specification continues.

The operator's free hand can be used to guide the camera distally over the cuspid and molar areas, until the buccal surface of the subject's last tooth in the back of the mouth and in the upper quadrant is recorded. The camera lens is angled to capture the full biting surface of this same last back tooth, pausing 1-2 seconds over the biting surface of each tooth (or alternatively the camera does not need to be paused over the tooth surface), and moving the camera over the molar and cuspid areas, thus guiding the camera towards the lateral and central incisor areas until the biting surface of the subject's first front tooth in the upper quadrant is recorded.

The camera lens is then angled to record the lingual surface of this same first front tooth, pausing 1-2 seconds over the lingual surface of each tooth (or alternatively the camera does not need to be paused over the tooth surface), and moving the camera over the central and lateral incisor area, thus guiding the camera distally over the cuspid and molar areas until the lingual surface of the subject's last back tooth in this upper quadrant is recorded. On the same side of the mouth, the camera is moved down to record the buccal surface of the subject's last back tooth in the lower quadrant, pausing 1-2 seconds over the buccal surface of each tooth (or alternatively the camera does not need to be paused over the tooth surface), and moving the camera over the molar and cuspid areas in the lower quadrant.

The operator can then use a free hand to move the lower lip down to expose and record the full buccal surface of each tooth in the lateral and central incisor area, until the subject's first front tooth in the lower quadrant is recorded. The camera lens is angled to capture the full biting surface of this same front tooth, pausing 1-2 seconds over the biting surface of each tooth (or alternatively the camera does not need to be paused over the tooth surface), and moving the camera over the central and lateral incisor areas, thus guiding the camera distally over the cuspid and molar areas until the biting surface of the last tooth in the back of the subject's mouth in the lower quadrant is recorded. The camera lens is then angled to begin recording the lingual surface of this same last back tooth, pausing 1-2 seconds over the lingual surface of each tooth in the molar and cuspid areas (or alternatively the camera does not need to be paused over the tooth surface), and guiding the camera over the lateral and central incisor areas until the subject's first front tooth in this lower quadrant is recorded.

If a mouth prop is being used, move it to the opposite side to continue recording. The foregoing sequence of video recording is then repeated on the opposite side of the subject's mouth. Once the recording of every tooth surface is complete, recording can be stopped. If needed, the mouth prop can be removed and placed inside a sealable biohazard bag for transport to the lab to be cleaned and sterilized.

Similar to video recordings, single frame images can be obtained in any suitable way. The following is an exemplary step-by-step methodology for taking these digital images. The subject's full set of teeth can be visualized in six sections. These sections include an upper right, lower right, upper middle, lower middle, upper left, and lower left. The operator's free hand can be used to lift the subject's upper lip to expose the full buccal surface of the central and lateral incisors. In camera mode, along with the intra-oral setting, a digital image of up to 6 teeth is captured in each section on the buccal side and again on the lingual side for a total of 12 digital images that represent all tooth surfaces in that particular quadrant.

At the completion of video or camera recordings of all tooth surfaces, the subject's file is saved and closed, to be prepared and analyzed at a later time. In preparation for analysis, single still frame digital images of each tooth surface can be produced from the video recording with digital imaging software. Secure storage of these video files and single image files make it possible to maintain archival data that can be better subjected to additional analysis and reliability determinations.

Analyzing Data

Generally, to calculate the percentage of plaque in a given image, the image of the tooth is cropped, so that the image only includes the targeted tooth in the image without losing the integrity of the tooth. Imaging software is then used to lower the resolution. The image is resized to a percentage of 50 or less (or to reset the pixel to 100 in horizontal percentage, and the vertical percentage will be automatically adjusted). The R program is then run to obtain the plaque percentage for the tooth (see FIG. 5 for the R code to obtain the final plaque percentage for the tooth).

More specifically as it pertains to the step of the R program obtaining the plaque percentage, to digitize the color, most software programs use three dimensions to record the color, namely the RGB. The software programs score the value of a specific pixel on each dimension, and a three-dimensional point (x, y, z) uniquely defines the color of the specific pixel. The software uses two digits for each color dimension, and each digit uses a hexadecimal system to count the numbers. Therefore, there are 256 possible values to score each dimension of the color. Since an objective herein was to calculate the percentage of plaque on a tooth and a typical plaque is always presented in a yellow color, the calculated score was used to judge whether each pixel should be classified as yellow or not.

The determination of whether a pixel should be considered yellow can be achieved and implemented in any suitable manner. For example, as described herein for illustrative purposes, the combinations of the three colors (RGB) that can create 'yellow' were determined quantitatively. Each color dimension was divided into four categories: (0, 64), (64, 128), (128, 192), (192, 255). Four categories were chosen because that was considered an acceptable compromise for accuracy and computational difficulty. Thus, in total, the end result was 64 categories. Next, the middle point of each range was chosen—32, 96, 160, 224—to be the representative of that range; the color for that specific combination was used to represent the color for that category. For example, for the category (0, 64) in red, (0, 64) in blue and (0, 64) in green, the color of point (32 in red, 32 in blue, and 32 in green) was used to represent the color for that category. After all 64 categories were scored, it was found that there were several common properties shared for those categories that are identified as yellow. These common properties are listed as follows:

1. The value of the red dimension was found to be between about 0.75 times of the value of the green dimension and about 2.5 times of the value of the green dimension.

2. The value of both the green dimension and the red dimension were found to be at least about 1.2 times of the value of the blue dimension.

Accordingly, if the values of the pixel met the conditions above, it was classified as yellow. If not, the pixel was not classified as yellow. After results were obtained for each pixel, the percentage of yellow could be calculated by using the number of yellow pixels divided by the total number of pixels in the picture. FIG. 6 depict color samples that can be classified as 'yellow' color (plaque) or non-yellow color (normal).

Automated Selection

Figure 7:
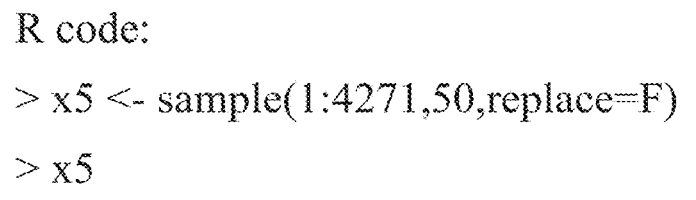

As it pertains to video recordings, each recording is broken down into individual frames. A random number generator is then used to randomly select a predetermined number of frames (e.g., 50) from one (1) to x, where x is the number of total images/frames within that recording. The R code for this can be seen in FIG. 7. Generally, frames can be randomly selected with or without specified criteria for the selection of frames. These criteria (e.g., a predetermined number of frames from each quadrant, certain quality of the frame to minimize the noise, etc.) can be inputted manually or can be learned automatically by the software algorithm, for example via artificial intelligence. If any criteria are present, the imaging software can automatically select frames that are relevant and/or discard frames that are not relevant. In any case, upon selection of the frames from the video recording, the corresponding images from the individual frames are selected, and the yellow percentage of the selected images are the calculated, as previously discussed.

Any suitable methodology for randomly selecting frames/images from the video recording is contemplated herein. For illustration purposes, differing methodologies were tested herein for this random selection. First, the 50 images can be randomly selected, but only the portion of the image related to teeth for analysis, is selected and cropped, as previously discussed. Another methodology is selecting images from the middle 60% of the complete video recording, thus truncating the first 20% and the last 20% of the video recording. Yet another methodology is simply randomly selecting 50 images from the frames of the video recording. Finally, each tooth can be selected, cropped, and analyzed separately, and subsequently taking the average of the scores of the teeth.

TABLE 1

Dental plaque percentage comparison using different methods.

| Subject ID and Intervention Day | Random Selection with selecting and cropping | Random Selection with truncation | Random Selection Results | Individual Evaluation Results (Benchmark) |
| --- | --- | --- | --- | --- |
| 1002-P3 | 0.0599 | 0.0981 | 0.0948 | 0.1571 |
| 1008-P5 | 0.0472 | 0.0465 | 0.1044 | 0.1163 |
| 1009-P5 | 0.0365 | 0.0500 | 0.0444 | 0.0481 |
| 1011-P5 | 0.4047 | 0.3899 | 0.3075 | 0.3611 |
| 1027-P3 | 0.0438 | 0.0220 | 0.0403 | 0.1127 |
| 1034-P3 | 0.1715 | 0.1364 | 0.1380 | 0.1757 |
| 1042-P5 | 0.3054 | 0.2293 | 0.2293 | 0.4311 |
| 1045-P3 | 0.0768 | 0.0861 | 0.09609 | 0.0424 |
| 1047-P3 | 0.0560 | 0.0375 | 0.08125 | 0.0531 |
| 1050-P3 | 0.1042 | 0.0500 | 0.03780 | 0.2149 |

Hardware and Software Infrastructure Examples

The present invention may be embodied on various computing platforms that perform actions responsive to software-based instructions and most particularly on touch-screen portable devices. The following provides an antecedent basis for the information technology that may be utilized to enable the invention.

The computer readable medium described in the claims below may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any non-transitory, tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wire-line, optical fiber cable, radio frequency, etc., or any suitable combination of the foregoing. Computer program code for carrying out operations for aspects of the present invention may be written in any combination of one or more programming languages, including an object oriented programming language such as Java, C#, C++, Visual Basic or the like and conventional procedural programming languages, such as the "C" programming language or similar programming languages.

Aspects of the present invention are described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

It should be noted that when referenced, an "end-user" is an operator of the software as opposed to a developer or author who modifies the underlying source code of the software. For security purposes, authentication means identifying the particular user while authorization defines what procedures and functions that user is permitted to execute.

GLOSSARY OF CLAIM TERMS

About: This term is used herein to refer to approximately or nearly and in the context of a numerical value or range set forth means ±15% of the numerical. In an embodiment, the term "about" can include traditional rounding according to significant figures of the numerical value. In addition, the phrase "about 'x' to 'y'" includes "about 'x' to about 'y'".

Frame: This term is used herein to refer to a fraction/division of time on a multimedia (e.g., video) timeline.

Oral health: This term is used herein to refer to the well-being of one's mouth, specifically based herein on the plaque that may be present in the person's mouth. More specifically, the manner in which plaque affects oral health can be the magnitude and ratio of dental plaque per tooth and across all teeth, the estimated age of dental plaque per tooth and across all teeth, and the ratio of plaque burden to plaque age per tooth and across all teeth.

Random selection: This term is used herein to refer to a relatively unpredictably chosen array of frames/images from a video recording. The term "relatively" is used because it is contemplated herein that this random selection can be performed with or without a predetermined set of criteria for the selection. For example, if 1,000 frames are present in a video recording, a set of criteria may eliminate 200 of those frames, and then 50 frames can be "randomly selected" from the remaining 800 frames. Alternatively, the 50 frames can be "randomly selected" from the 1,000 frames with no criteria present. Both circumstances are contemplated herein.

Single still frame digital image: This term is used herein to refer to a visual representation of a tooth extracted at a specific time during a video recording.

Substantially all: This term is used herein to refer to a representative number of tooth surfaces that, when analyzed, can be used to characterize the amount of plaque across all teeth or on each tooth. This number can be all teeth in the subject's mouth, or it can be an amount less than all of the teeth. For example, some teeth may be inaccessible by an intraoral camera due to the anatomy of a particular subject's mouth, so only the accessible surfaces are recorded. These circumstances are still considered herein as "substantially all".

The advantages set forth above, and those made apparent from the foregoing description, are efficiently attained. Since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention that, as a matter of language, might be said to fall there between.

What is claimed is:

1. A method of assessing oral health in a patient or subject, comprising the steps of:
    providing an intraoral camera that can capture or record frames within a mouth of said subject;
    using the intraoral camera, capturing or recording the frames of substantially all buccal, occlusal, and lingual surfaces in the subject's set of teeth, the captured frames selected by the group consisting of photographs and video recordings;
    importing the captured frames into an image processing software program implemented on a computing device;
    processing the captured frames on the image processing software program to generate images of the teeth to be analyzed;
    cropping at least one of the captured frames such that the cropped captured frame includes a targeted tooth;
    analyzing and classifying color of the cropped at least one of the captured frames by:
        classifying the color of each pixel of the captured frame using red-green-blue color dim code combinations to determine presence of yellow color, wherein a three-dimensional point (x, y, z) defines the color of each pixel;
        dividing each color of the red-green-blue color code combinations into four categories, wherein the four categories are (0, 64), (64, 128), (128, 192), and (192, 255);
        selecting a middle point in each category to be representative of the corresponding category, and
        scoring all categories to determine when the yellow color is present in one or more pixels, wherein the yellow color is present in one or more pixels when a value of a red dimension is between about 0.75 times of a value of a green dimension and about 2.5 times of the value of the green dimension, and when the values of the green and red dimensions are at least about 1.2 times a value of a blue dimension, wherein the yellow color indicates presence of plaque; and
    scoring results of the color analysis to objectively and quantitatively assess the oral health of the subject.

2. A method as in claim 1, further comprising the steps of positioning a dental barrier over a lens of the intraoral camera and positioning a camera tip of the intraoral camera over the dental barrier.

3. A method as in claim 1, further comprising the step of dividing the subject's set of teeth into a plurality of sections, wherein the sections include an upper right section, a lower right section, an upper middle section, a lower middle section, an upper left section, and a lower left section.

4. A method as in claim 1, wherein the step of processing the frames is further performed by lowering a resolution of the image to a percentage of about 50 or less.

5. A method as in claim 1, wherein the step of scoring the results of the color analysis includes calculating a percentage of the yellow color by dividing a number of yellow pixels by a total number of pixels in the image.

6. A method as in claim 1, further comprising the step of dividing the subject's set of teeth into a plurality of quadrants, wherein the quadrants include an upper right quadrant, a lower right quadrant, an upper left quadrant, and a lower left quadrant.

7. A method as in claim 6, wherein the step of capturing or recording the frames includes capturing and recording video of the tooth surfaces in at least one upper quadrant and in at least one lower quadrant.

8. A method as in claim 6, wherein the step of capturing or recording the frames includes capturing and recording video of the buccal surfaces in a quadrant, followed by capturing and recording video of the occlusal surfaces in the quadrant, followed by capturing and recording video of the lingual surfaces in the quadrant, and followed by repeating the foregoing steps in another quadrant.

9. A method as in claim 1, wherein the step of processing the frames on the image processing software program includes extracting single still frame digital images of the tooth surfaces from the video recording.

10. A method as in claim 9, further comprising the step of randomly selecting a plurality of frames from all of the captured frames prior to processing the frames on the image processing software program, wherein the random selection of the plurality of frames is performed with or without criteria for the random selection.

11. A method of assessing oral health in a patient or subject, comprising the steps of:
   providing an intraoral camera that can capture or record frames within a mouth of said subject;
   positioning a dental barrier over a lens of the intraoral camera and positioning a camera tip of the intraoral camera over the dental barrier;
   dividing the subject's set of teeth into a plurality of quadrants, wherein the quadrants include an upper right quadrant, a lower right quadrant, an upper left quadrant, and a lower left quadrant;
   using the intraoral camera, capturing or recording the frames of substantially all buccal, occlusal, and lingual surfaces in the subject's set of teeth,
   wherein the captured frames are video recordings,
   wherein the step of capturing or recording the frames includes capturing and recording video of the tooth surfaces in at least one upper quadrant and in at least one lower quadrant,
   wherein the step of capturing or recording the frames includes capturing and recording video of the buccal surfaces in a quadrant, followed by capturing and recording video of the occlusal surfaces in the quadrant, followed by capturing and recording video of the lingual surfaces in the quadrant, and followed by repeating the foregoing steps in another quadrant;
   importing the frames into an image processing software program implemented on a computing device;
   randomly selecting a plurality of frames from all of the captured frames, wherein the random selection of the plurality of frames is performed with or without criteria for the random selection;
   processing the frames on the image processing software program to generate images of the teeth to be analyzed,
   wherein the step of processing the frames on the image processing software program includes extracting single still-framed digital images of the tooth surfaces from the video recording,
   wherein the step of processing the frames is performed by cropping each image such that the image includes a targeted tooth in the image and lowering a resolution of the image to a percentage of about 50 or less;
   analyzing and classifying color of at least a plurality of the frames to determine presence of yellow color, wherein the yellow color indicates presence of plaque,
   wherein the step of analyzing and classifying the color is performed by classifying the color of each pixel of the image, wherein the color of the each pixel is classified using red-green-blue color code combinations, wherein a three-dimensional point (x, y, z) defines the color of the each pixel, wherein the step of analyzing and classifying the color is further performed by:
      dividing each color dimension of the red-green-blue color code combinations into four categories, wherein the four categories are (0, 64), (64, 128), (128, 192), and (192, 255),
      selecting a middle point in each category to be representative of the corresponding category, and
      scoring all categories to determine when the yellow color is present on the each pixel,
   wherein the yellow color is present on the each pixel when a value of a red dimension is between about 0.75 times of a value of a green dimension and about 2.5 times of the value of the green dimension, and when the values of the green and red dimensions are at least about 1.2 times a value of a blue dimension;
   scoring results of the color analysis to objectively and quantitatively assess the oral health of the subject,
   wherein the step of scoring the results of the color analysis includes calculating a percentage of the yellow color by dividing a number of yellow pixels by a total number of pixels in the image.

* * * * *